United States Patent [19]

McCoy

[11] Patent Number: 4,900,320

[45] Date of Patent: Feb. 13, 1990

[54] SANITARY NAPKIN WITH PANTY GATHERING FLAPS

[75] Inventor: Sherilyn S. McCoy, Monmouth Junction, N.J.

[73] Assignee: McNeil-PPC, Inc., Milltown, N.J.

[21] Appl. No.: 874,978

[22] Filed: Jun. 16, 1986

[51] Int. Cl.⁴ .............................................. A61F 13/16
[52] U.S. Cl. ..................................... 604/387; 604/389
[58] Field of Search ................ 604/386, 387, 389, 390

[56] References Cited

U.S. PATENT DOCUMENTS 4,285,343  8/1981  McNair ............................... 604/387
4,608,047  8/1986  Mattingly ............................ 604/387

*Primary Examiner*—C. Fred Rosenbaum
*Assistant Examiner*—Sharon Rose

[57] ABSTRACT

An improved sanitary napkin is provided which protects the user's undergarment from wetting. The napkin is provided with two flaps each affixed to the garment facing side of the napkin and each extending in a direction tranverse to the longitudinal edge of the napkin and adapted to encircle the crotch portion of the undergarment. The flaps are affixed to the garment facing side of the napkin at an affixation point inward from the longitudinal edge of the napkin so that when encircling the crotch portion, the edges of the crotch portion of the undergarment are gathered under the napkin and the napkin acts as a shield to prevent wetting.

7 Claims, 3 Drawing Sheets

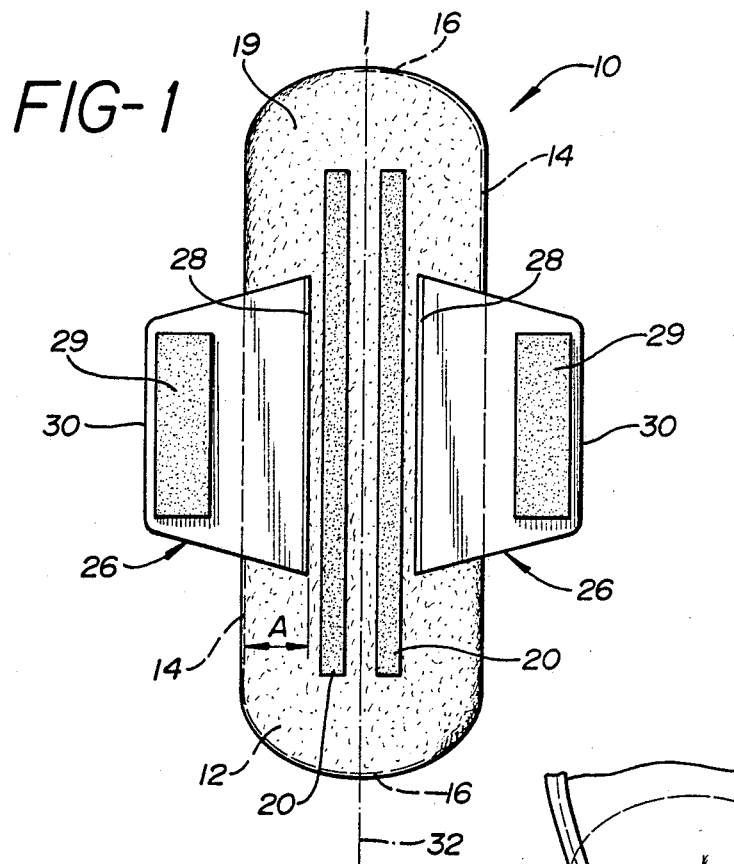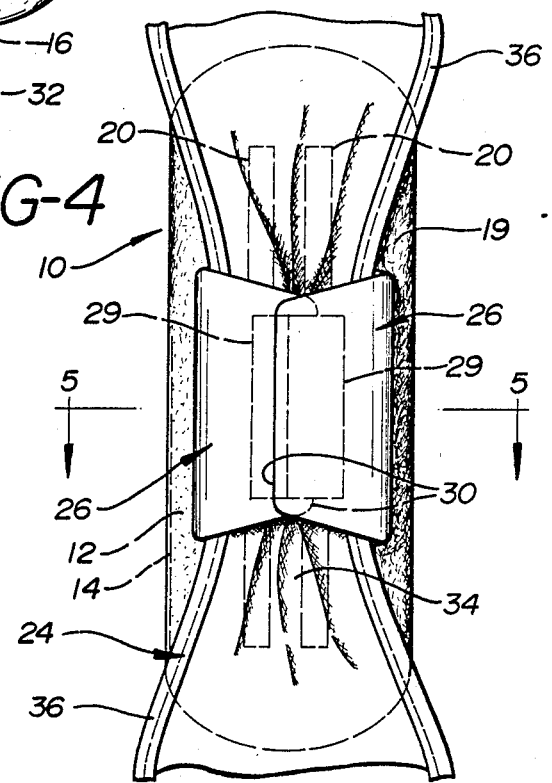

SANITARY NAPKIN WITH PANTY GATHERING FLAPS

BACKGROUND OF THE INVENTION

This invention relates to an absorbent product for absorbing body fluids and in particular, to such a product to be worn against the perineal portion of the body and held in place by attachment to the crotch portion of the undergarment worn by the user. Such products are now in wide use as sanitary napkins, panty shields, panty liners and adult incontinence pads. While this invention is directed to all such products, for purposes of simplification, these products will be referred to herein simply as napkins.

Typically, these napkins comprise a generally elongated absorbent element such as a pad of absorbent material, having a body facing side, a garment facing side, longitudinally extending edges and lateral ends. The absorbent element is usually provided with a body fluid pervious cover on the body facing side and a body fluid impervious cover on the garment facing side which latter cover may be exposed or may be provided with a further overlying layer. These prior products are held in place by providing an area or areas of pressure sensitive adhesive on the garment facing side to adhere to the inner crotch surface of the wearer's undergarment. A great number of suggestions and patents exist which suggest varying configurations of pressure sensitive adhesive applications in such products. Examples of such suggestions are found in U.S. Pat. Nos. 3,913,580; 3,897,783 and 3,888,255.

While in the main, such prior products have performed well, remaining in place and providing the user with ease of placement and removal, these products have suffered from certain drawbacks. For example, the inner crotch surface to which these products are adhered is constantly being distorted, twisted and stretched due to the movements of the wearer. As a result, frequently, the adhesive attachment detaches with the undesirable result of the napkin's moving out of place. Further, while the napkin frequently reattaches owing to the continuing adhesive nature of the pressure sensitive adhesive, reattachment often places the napkin in an undesirable position wherein the napkin does not function properly. In an extreme case, detachment of the adhesive also results in the adhesive folding over on itself and then becoming unavailable for reattachment.

Further, it has been discovered that, in the event that the inner crotch becomes moist for one reason or another, the adhesive attachment is greatly weakened and misplacement of the napkin results.

Still another drawback related to prior napkins occurs. It has been discovered that often, in the course of wearing a napkin, the edges of the crotch of the panty tends to enfold onto the body facing surface of the napkin. In such a position, the panty is likely to be wetted with body fluid, either emanating from the napkin or deposited from the body itself.

This latter problem has been addressed to some degree in U.K. Pat. No. 2 048 684 wherein a sanitary towel has been provided with flaps extending along the longitudinal edges of the absorbent element. These flaps appear to protect portions of the inner crotch of the undergarment adjacent to the absorbent element but do not provide any means for avoiding fold over of the panty. Nor does the U.K. Patent in any way address the problems of attachment outlined above.

In U.S. Pat. Nos. 2,387,271; 3,397,697; 4,285,343 and in European Pat. application No. 0130848, napkins have been suggested comprising a central absorbent pad having lateral flaps extending from the longitudinal edges of said pad. As is suggested in all but U.S. Pat. No. 2,787,271, the lateral flaps may now be folded around the crotch portion of the undergarment and affixed in placed on the outer crotch portion. Accordingly, the edges of the crotch of the undergarment are completely covered by the flaps and protected from staining or wetting with menstrual fluid.

While these latter suggestions indeed protect the wearers undergarment, unfortunately they do not completely protect the wearer. For example, in the last two cited references, the flaps are covered with an absorbent material. Accordingly, fluid striking the center of the pad may now wick from the pad to the flaps and then onto the wearers thighs where such fluid could stain the wearer's outer garment. Further, even if the flaps comprise a non-wicking medium, fluid reaching the flaps has a clear path of flow onto the thighs of the wearer.

Accordingly, there is a need for a more protective sanitary napkin.

SUMMARY OF THE INVENTION

It has now been discovered that the above recited shortcomings of prior sanitary napkins may be obviated by providing a napkin of an improved construction. Specifically, my improved napkin comprises a central absorbent element having generally longitudinally extending edges, a body facing side and a garment facing side. The garment facing side is provided with a menstrual fluid impervious cover or barrier layer and, optionally, the body facing side is provided with a menstrual fluid permeable cover which may also extend over the longitudinal edges and even over the barrier layer to completely enclose the absorbent element.

In accordance with the teachings of this invention, two flaps are provided on the garment facing side of the napkin. The flaps are each affixed at one end thereof to the garment facing side of the napkin with the other, free end, extending laterally in a direction tranverse to the longitudinal edge of the napkin. The flaps are adapted to encircle the crotch portion of the undergarment once the napkin has been placed on the inner crotch portion and then be affixed to the outer crotch portion.

When the napkin is so emplaced, it is important that no path be provided which will allow fluid deposited on the body facing side of the napkin to be transported to the undergarment or to the thighs of the wearer. To this end, it has been discovered that the affixed end of each flap must be affixed to the garment facing side of the napkin at an affixation point which is inward from the longitudinal edge of the napkin. In this way, the napkin itself acts as a shield preventing the undesirable transportation of fluid. Preferably the flaps are affixed inward of the longitudinal edge of the napkin by a distance of at least one eight of an inch, e.g., one quarter of an inch.

In a preferred embodiment, one or more of the flaps are provided with pressure-sensitive adhesive for affixing the flaps in the crotch encircling position. Similarily, the garment facing side of the napkin may be provided with pressure-sensitive adhesive for affixing the napkin to the inner crotch portion of the undergarment.

BRIEF DESCRIPTION OF THE DRAWINGS

FIG. 1 is a plan view of the garment facing side of a sanitary napkin embodying the teachings of this invention;

FIG. 4 is a plan view of the garment facing side of the napkin of FIG. 1 emplaced in the crotch portion of an undergarment;

DETAIL DESCRIPTION OF THE INVENTION

Figure 2:
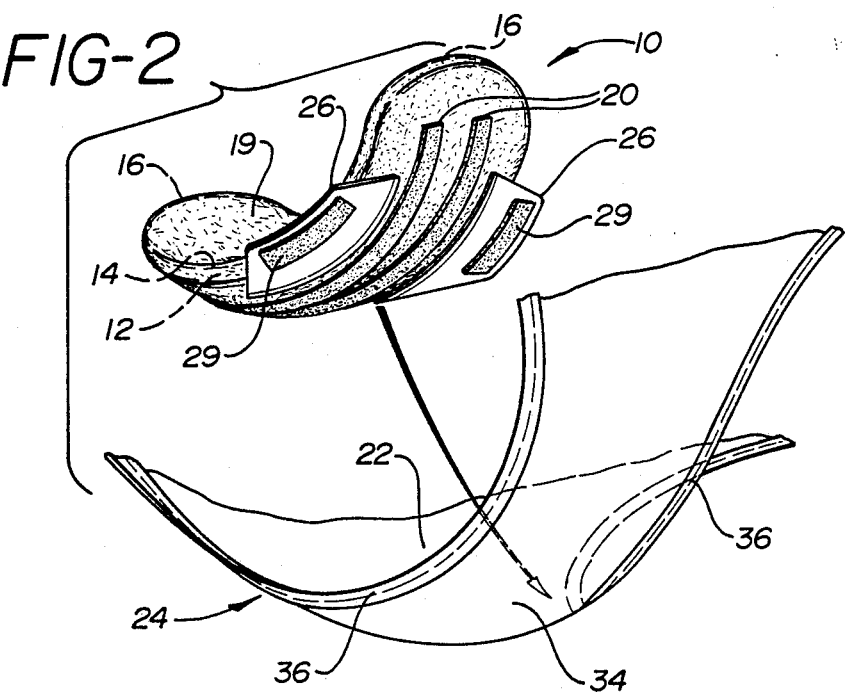
FIG. 2 is a perspective view of the napkin of FIG. 1, as it is about to be emplaced in the crotch portion of an undergarment.

Referring now to the drawings, FIGS. 1 through 5 illustrate a sanitary napkin 10 embodying this invention.

The napkin 10 is provided with a centrally located absorbent element 12 having generally longitudinally extending edges 14 and transversely extending ends 16. The absorbent element 12 may be comprised of any of the well known absorbent materials used in products for absorbing body fluids such as, for example, loosely associated absorbent hydrophilic materials such as cellulose fibers, e.g., wood pulp, regenerated cellulose or cotton fibers. Such fibers may be chemically or physically modified and the absorbent element may include such fibers in combination with other materials, both natural and synthetic, such as hydrophilic foams, hydrophilic polymers or the like. Wood pulp is the material of choice primarily because it is inexpensive and readily available.

The absorbent element may also comprise layers of materials which in the aggregate are body fluid absorbent. For example, the outer most layer (closest to the body) may be resilient, relatively non-absorbing, fluid pervious material. Such a material is provided for comfort and comformability and directs fluid to an underlying layer, e.g., wood pulp, which retains such fluid. A useful material for this outer layer comprises hollow polyester fibers.

Figure 5:
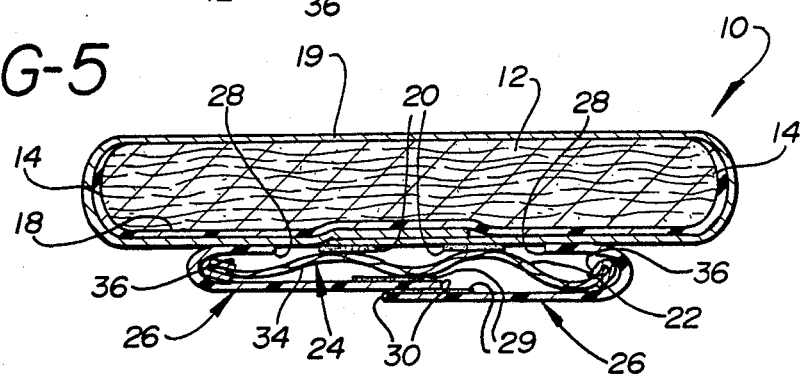
FIG. 5 is a cross-sectional view of the emplaced napkin of FIG. 4, taken along line 5—5.

For simplicity and as best viewed in FIG. 5, the absorbent element 12 is simply illustrated as a pad of wood pulp fibers.

Again as best viewed in FIG. 5, underlying the garment facing surface of the absorbent element 12 is a body fluid impervious barrier 18 provided to preclude body fluid from passing onto the undergarment of the wearer. Barrier 18 may be any polymeric film such as polyethylene, polypropylene or cellophane or may be a normally fluid-pervious material that has been treated to be impervious such as fluid repellent paper. Barrier 18 may also be of the so-called breathable barrier materials which allow for the transportation of gases and vapors but impede the transport of liquids. Examples of such are repellent treated tissue paper and microporous polymeric films.

As shown in FIG. 5, the barrier 18 not only overlies the garment facing side of the absorbent element 12 but also extends to overlie the longitudinal edges 14. This configuration is preferably provided to prevent failure of the napkin by fluid passing from the napkin via the edges 14 although it will be understood that only some or none of the edges 14 need be covered by the barrier 18 in order to have a functional napkin.

A fluid permeable cover 19 is provided, overlying the body facing side of the absorbent layer, the barrier covered edges, and the garment facing side of the absorbent element 12. This cover may comprise any of the well known cover materials used in sanitary napkins, including, for example, nonwoven fabrics of cellulose, regenerated cellulose, polyester or other synthetic polymers. Additionally, polymer films having apertures therethrough to render the films pervious to fluids may also be employed.

A particularly useful material may be a fabric comprised of heat bondable polyester/polyethylene conjugate fibers. Such conjugate fibers are fibers which comprise a polyester core surrounded by a sheath of polyethylene. Preferably the conjugate fibers employ high density polyethylene, that is, linear polyethylene having a density of at least 0.94 gm/cc and a Melt Index (as determined by ASTM D-1288E method, employing the parameters of 190° C. and 2160 gms.) of greater than 1, preferably greater than about 10, and more preferably from 20 to about 50. The fibers may comprise from about 40 to 60 percent, by weight polyester and preferably, from 45 to 55 percent by weight polyester, with the remainder being polyethylene. Such fibers may be used in denier of from 1 to about 6 and may be from about ½ inch (1.27 cm.) to about 3 to 4 inches (7.62 to 10.16 cm.) long. The fabric comprising such fibers is stabilized by applying heat thereto whereby thermal bonding takes place.

Preferably the garment facing side of the napkin is further provided with pressure-sensitive adhesive means 20 for adhering the napkin to the inner crotch portion 22 of a panty 24, as is well known in connection with prior art napkins. The pressure-sensitive adhesive means 20 may take various forms, i.e., stripes, bands, patches or the like, and is preferably protected, prior to use, by a release strip of silicone coated paper or the like (not shown).

In accordance with the teachings of this invention, affixed to the garment facing side of the napkin are two laterally extending flaps 26. Specifically, one affixed end 28 of each flap is affixed to the garment facing side of the napkin and the other free end 30 extends laterally in a direction transverse to the longitudinal edge 14 of the absorbent element. As will be further described, the flaps 26 are adapted to encircle the crotch of the undergarment once the napkin has been placed on the inner crotch portion 22 and then affixed to the outer crotch portion. To this end, pressure-sensitive means 29 are provided on the flaps 26. Such means may be, for example, patches or bands of pressure-sensitive adhesive and may be protected by release material (not shown) prior to use.

For reasons best understood in connection to description following hereinafter, it is important that the affixed end 28 be affixed to the garment facing side of the napkin at an affixation point which is inward from the longitudinal edge of the napkin and that the portion of the flap 26 which extends laterally from the point of affixation to the free end 30 of the flap 26 be unaffixed. In particular, it is important that the flaps 26, when extended laterally have a portion between the affixation point and the longitudinal edge 14 of the absorbent element (shown as A in FIG. 1) which is unaffixed to the garment facing side of the napkin. While many of the benefits of this invention will inure by affixing each flap as far inward from the edge 14 as to the longitudinal centerline 32 of the napkin, the affixation point may be as little as one-eighth of an inch inward of the edge 14 (i.e., the dimension A should equal at least ⅛ inch) and preferably at least one quarter inch inwardly of the edge 14.

Figure 3:
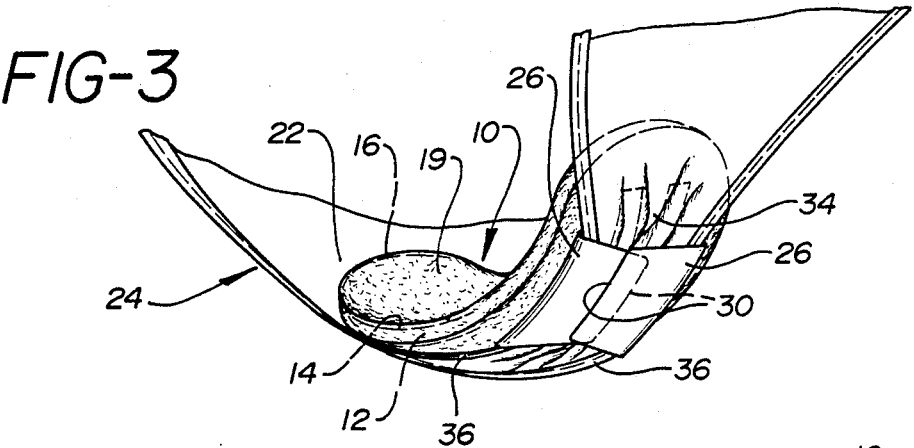
FIG. 3 is a perspective view of the napkin of FIG. 1 fully emplaced in the crotch portion of an undergarment.

To best understand the importance of the parameters set out above and the advantages which accrue with respect to use of this invention, reference is now made to FIGS. 2 through 4 which illustrate the employment of the napkin 10 into the crotch portion 24 of an undergarment.

In FIG. 2, an exploded perspective view, the napkin 10 is emplaced into the inner crotch portion 22 of undergarment 24. The pressure-sensitive adhesive means 20 are pressed against the inner crotch portion 22 to aid in holding the absorbent element 12 firmly in place. This is best accomplished by emplacing the napkins while the user's undergarment is in a lowered position. Once the napkin is firmly emplaced in the inner crotch portion, the flaps 26 are then to be folded about the crotch portion so as to overlie the outer crotch portion 34 of the undergarment and be secured in such position. This step is best accomplished by the user's raising the undergarment into its normal wearing position, then folding the flaps about the outer crotch portion, and then securing the flaps into position by employing the pressure-sensitive adhesive means 29.

As may best be appreciated from a study of FIGS. 3 through 5, by virtue of the affixation of the flaps inward of the longitudinal edges 14 of the absorbent element, when the flaps encircle the crotch portion of the undergarment, the flaps will draw the panty edges 36 inwardly of the edges 14 and beneath the absorbent element 12 and tend to form gathers in the encircled crotch portion.

Several advantages occur. Firstly, of course, the encircling flaps, secured in place by the adhesive means 29, prevent the panty edges 36 from folding over onto the body facing side of the napkin where the panty might otherwise be subject to wetting. Beyond this however, by having those panty edges drawn together beneath the absorbent element and its protective barrier 18, the napkin itself acts as a shield to completely insure that this portion of the undergarment is not vulnerable to wetting.

Still another benefit occurs when, as in the usual case, the panty edges comprise elastic material provided to insure good fit. By following the teachings of this invention, these elastic panty edges are now drawn inwardly and directly under the absorbent element. Thus, when the panty is drawn up to the normal wearing position, the elastic edges now exert an upward force against the absorbent element 12, urging the absorbent element into close contact with the body and hence insuring that fluid discharged from the body will strike the absorbent element. This beneficial result is to be contrasted with prior suggestions wherein the elastic edges of the panty lie beyond each longitudinal edge 14 of the absorbent element and hence the napkin is supported only loosely within the crotch of the undergarment.

It will be appreciated that while the width of the crotch portion of the panty will vary widely from one undergarment design to another, the napkin of this invention will be equally usable with each of such designs. Irrespective of the width of the crotch portion, the flaps may be overlapped in the encircling position to whatever degree is required to draw the panty edges 36 inwardly of the absorbent element edges 14 and hence give the advantages described herein.

From the foregoing it is apparent then, that a considerably wide choice of materials may be employed in constructing the flaps provided however that such material is sufficiently strong and flexible to hold the napkin in the emplaced position. Thus, for example, woven and nonwoven fabrics, polymeric films or any combinations thereof may be employed such as the materials already being employed in sanitary napkins as covers and barriers. Aside from the above considerations, the choice of method of affixing the flaps to the garment facing side of the napkin may dictate the materials of construction chosen. For example, if the flaps are adhered to the napkin by use of construction adhesives, the choice of materials must be such as to get a compatible and sufficiently strong bond. Should it be desired to affix the flaps via heat sealing or sonic sealing techniques then such methods would dictate employing thermoplastic materials. A material of choice is polyethylene film which is both readily available and inexpensive and, in thickness of from 0.5 mil to 5.0 mils. is both sufficiently strong and flexible.

It will be understood that the affixation of the flaps to the garment side of the napkin may be along various patterns such as continuous lines of affixation, a discontinuous line or at a single point or spots or at several points. In this connection, when referring to a point of affixation being inward of the longitudinal edge of the napkin, it is meant the point of affixation closest to the longitudinal edge.

Referring now to FIGS. 6 through 9, various alternative embodiments are illustrated, wherein reference numerals referring to elements essentially common to those of FIGS. 1 through 5 have been identically employed.

Figure 6:
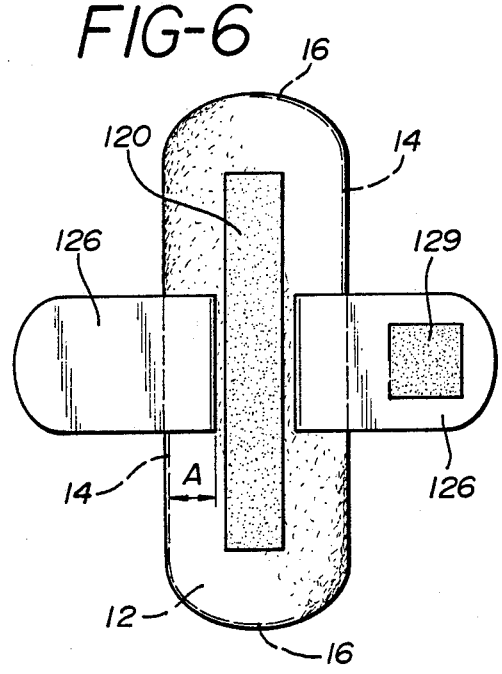
FIG. 6 is a plan view of the garment facing side of a napkin of this invention illustrating an alternative embodiment.

Referring to FIG. 6, as an alternate embodiment, it is noted that only one of the flaps 26 bears a pressure-sensitive adhesive element 29 and accordingly when the flaps are encircled about the crotch portion of the undergarment it is important that the non-adhesive bearing flap be first applied directly against the undergarment and then the adhesive bearing flap be overlapped and adhered onto the non-adhesive bearing flap. Also illustrated is a variation (one of many possible designs) in the shape of the flaps, in this case being essentially of uniform length in the longitudinal direction of the napkin. Further, as contrasted with the prior described embodiment, only one adhesive element 20 is provided on the garment facing side of the napkin.

Figure 7:
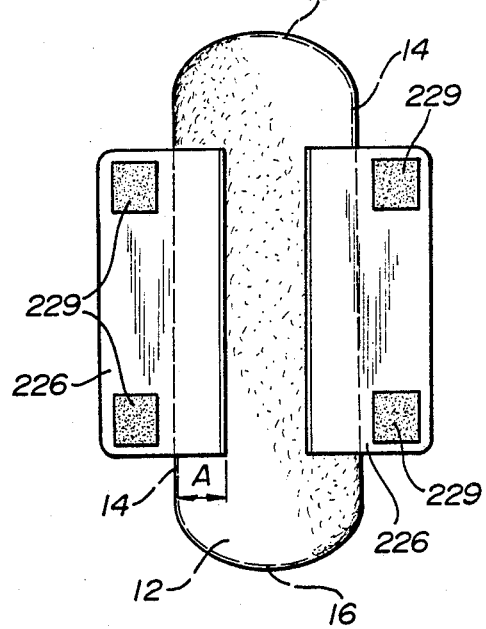
FIG. 7 is a plan view of the garment facing said of a napkin of this invention illustrating another alternative embodiment.

In FIG. 7, an embodiment is illustrated wherein the flaps are substantially longer in the longitudinal direction of the napkin. Accordingly, pressure-sensitive patches 29 have been provided at each free corner of the flaps to ensure that the encircled crotch portion is held by the flaps along the full longitudinal length of the flaps. It should be noted also that the pressure-sensitive adhesive employed in the other described embodiments has been dispensed with here.

Figure 8:
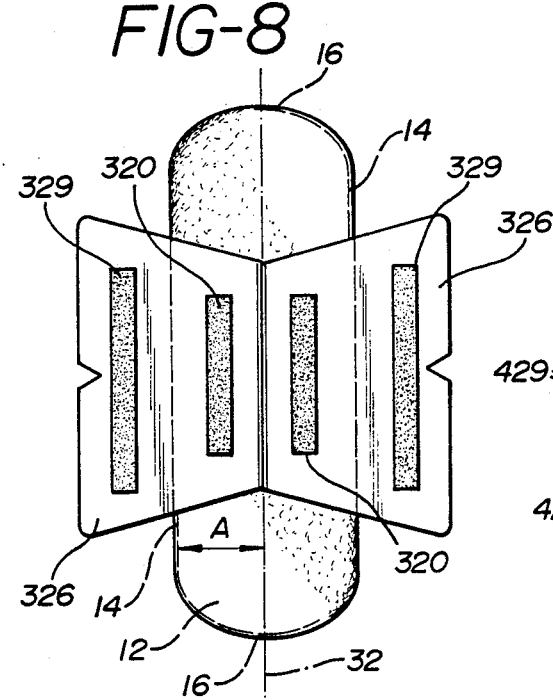
FIG. 8 is a plan view of the garment facing side of a napkin of this invention illustrating still another alternative embodiment.

FIG. 8 illustrates still another embodiment. In this embodiment the affixation point of the flaps coincides with the longitudinal center line 32 of the napkin. In fact, in one variation, the flaps are simply one unitary sheet affixed at its center to the garment facing side of the napkin with free ends extending laterally on either side. The flap pressure-sensitive adhesive elements 29 are provided in the form of longitudinally extending bands and, in the embodiment shown, the pressure-sensitive adhesive elements 20 are provided on that surface of the flaps which is intended to overlie the inner crotch portion of the undergarment.

Figure 9:
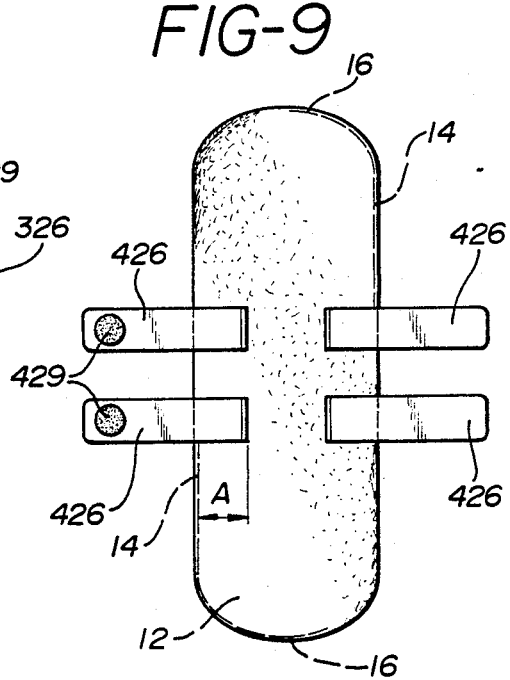
FIG. 9 is a plan view of the garment facing side of a napkin of this invention illustrating yet another alternative embodiment.

FIG. 9 illustrates yet another embodiment of this invention wherein the flaps each comprise two generally parallel stripes 26' having an attachment means 34 thereon. Such attachment means could be pressure-sensitive adhesive or alternatively could be any of the well known fastening means such as the so-called "Velcro" binders, buttons, snaps or the like.

To better illustrate the napkin of this invention, the following examples are provided.

EXAMPLE 1

A sanitary napkin having the general construction of that of FIGS. 1 through 5 is made. The absorbent element comprises a pad of wood pulp fluff, seven inches long, two and one half inches wide and 0.75 inches thick and weighing 9.7 grams. Overlying the garment facing surface and the longitudinal edges is a barrier layer comprising polyethylene film having a thickness of 0.5 mils. The pad and barrier are held together by an overwrapping tissue wrap and the tissue wrapped composite is enveloped by a nonwoven cover comprising fifty percent by weight polyester fibers and fifty percent by weight rayon fibers. Flaps having the trapezoidal shape shown in FIG. 1 are provided, the flaps being constructed of 2 mil polyethylene film having an embossment pattern imposed thereon for aesthetic purposes and to reduce stretch properties of the film. The long parallel edge of each trapezoidal flap measures four inches and is heat sealed parallel to the longitudinal edge of the wrapped absorbent element at a distance inward of said edge of one inch. The short parallel edge of each flap measures 2.75 inches and the two parallel edges of the individual flaps are spaced apart a distance of 2.5 inches whereby the flaps each extend laterally beyond the longitudinal edge of the absorbent element for a distance of one and one half inches. Each flap is provided, on the side to be pressed against the outer crotch portion of an undergarment, with a rectangular band of pressure-sensitive adhesive measuring 0.5 by 2 inches in the location illustrated in FIG. 1. The napkin, when emplaced, as described above, in the crotch of an undergarment completely protects the undergarment from wetting.

EXAMPLE 2

A sanitary napkin having the general construction of that of FIG. 6 is prepared. The absorbent element is of two layers: the body facing side comprising a pad of wood pulp measuring two and one half by seven inches by 0.35 inches and the garment facing side comprising a nonwoven heat bonded fabric of the conjugate fibers intermixed with resilient hollow polyester fibers, said fabric being coextensive with the wood pulp layer and weighing 4 oz/yd². This latter fabric is provided to give dimensional stability to the product. The composite absorbent element is wrapped in a cover of heat bonded conjugate fibers weighing 0.5 oz/yd². The garment facing side of the covered absorbent element is provided with a barrier layer comprising 2 mil thick polyethylene film. Flaps are provided of the shape illustrated in FIG. 6 and measuring two inches long in the dimension parallel with the longitudinal edge of the absorbent element and extending in the lateral direction, a distance of three inches. The flaps are heat sealed to the barrier layer along their two inch long edge at an affixation point 0.75 inches inwardly of the longitudinal edge of the absorbent element thereby extending beyond the longitudinal edge of the absorbent element for a distance of two and one quarter inches. One flap is provided with a patch of double faced tape measuring 1.5 inches square. The pads, when emplaced in the crotch portion of an undergarment, completely protect the undergarment from wetting.

What is claimed is:

1. An improved sanitary napkin comprising a central absorbent element and having generally longitudinally extending edges, a body facing side and a garment facing side;

said napkin provided with two flaps, each affixed at one end thereof to the garment facing side of the napkin with the remainder of the flaps freely extending laterally in a direction tranverse to the longitudinal edges of the napkin, said flaps adapted to encircle the crotch portion of the undergarment and provided with means for affixing said flaps in said encircling portion;

said flaps being affixed to the garment facing side of the napkin at an affixation point which is inward from the longitudinal edge of the napkin;

whereby when said flaps are affixed in said encircling position, the edges of the undergarment are gathered toward the longitudinal centerline of the napkin and are shielded from body fluids by the garment facing side of the napkin.

2. The napkin of claim 1 wherein said affixation point is at least one-eighth inch inward of said longitudinal edge.

3. The napkin of claim 2 wherein said affixation point is at least one quarter inch inward of said longitudinal edge.

4. The napkin of claim 1 wherein said means for affixing said flaps in said encircling position comprises pressure-sensitive adhesive means.

5. The napkin of claim 1 wherein said flap comprise polyethylene film having a thickness of from 0.5 to 5.0 mils.

6. The napkin of claim 1 wherein said flaps comprise a single sheet affixed to the garment facing side of the napkin at an affixation point generally central to the sheet wherein each portion of the sheet on either side of said affixation point constitutes each flap.

7. The napkin of claim 6 wherein said affixation point is essentially at the longitudinal centerline of the napkin.

* * * * *

US004900320C1

(12) REEXAMINATION CERTIFICATE (4389th)
United States Patent
McCoy

(10) Number: US 4,900,320 C1
(45) Certificate Issued: Jul. 3, 2001

(54) SANITARY NAPKIN WITH PANTY GATHERING FLAPS

(75) Inventor: Sherilyn S. McCoy, Monmouth Junction, NJ (US)

(73) Assignee: McNeil-PPC, Inc.

Reexamination Requests:
No. 90/003,637, Nov. 10, 1994
No. 90/004,088, Dec. 27, 1995

Reexamination Certificate for:
Patent No.: 4,900,320
Issued: Feb. 13, 1990
Appl. No.: 06/874,978
Filed: Jun. 16, 1986

(51) Int. Cl.[7] ............................. A61F 13/16; A61F 13/15
(52) U.S. Cl. .................... 604/387; 604/389; 604/385.04
(58) Field of Search ................... 604/385.1–391, 604/400–402

(56) References Cited

U.S. PATENT DOCUMENTS

| 2,662,527 | 12/1953 | Jacks | 128/290 |
|---|---|---|---|
| 2,787,271 | 4/1957 | Clark | 128/290 |
| 3,038,474 | 6/1962 | Harwood et al. | 128/288 |
| 3,073,309 | 1/1963 | Mosier | 128/290 |
| 3,397,697 | 8/1968 | Rickard . | |
| 3,406,689 | 10/1968 | Hicks et al. | 128/290 |
| 3,665,923 | * 5/1972 | Champaigne, Jr. | 604/387 |
| 3,888,255 | 6/1975 | Shah et al. . | |
| 3,897,783 | 8/1975 | Ginocchio . | |
| 3,913,580 | 10/1975 | Ginocchio . | |
| 4,285,343 | * 8/1981 | McNair . | |
| 4,324,246 | * 4/1982 | Mullane et al. . | |
| 4,589,876 | 5/1986 | Van Tilburg . | |
| 4,608,047 | * 8/1986 | Mattingly . | |
| 4,701,178 | 10/1987 | Glaug et al. | 604/387 |
| B1 4,589,876 | 5/1986 | Van Tilburg . | |

FOREIGN PATENT DOCUMENTS

| 3319421 | 11/1984 | (DE) . |
|---|---|---|
| 3326026 | 7/1985 | (DE) . |
| 0130848 | 9/1985 | (EP) . |
| 2 048 684 | 12/1980 | (GB) . |
| 5010718 | 4/1975 | (JP) . |
| 5213834 | 3/1977 | (JP) . |
| 60-158828 | 10/1985 | (JP) . |

* cited by examiner

*Primary Examiner*—John G. Weiss

(57) ABSTRACT

An improved sanitary napkin is provided which protects the user's undergarment from wetting. The napkin is provided with two flaps each affixed to the garment facing side of the napkin and each extending in a direction tranverse to the longitudinal edge of the napkin and adapted to encircle the crotch portion of the undergarment. The flaps are affixed to the garment facing side of the napkin at an affixation point inward from the longitudinal edge of the napkin so that when encircling the crotch portion, the edges of the crotch portion of the undergarment are gathered under the napkin and the napkin acts as a shield to prevent wetting.

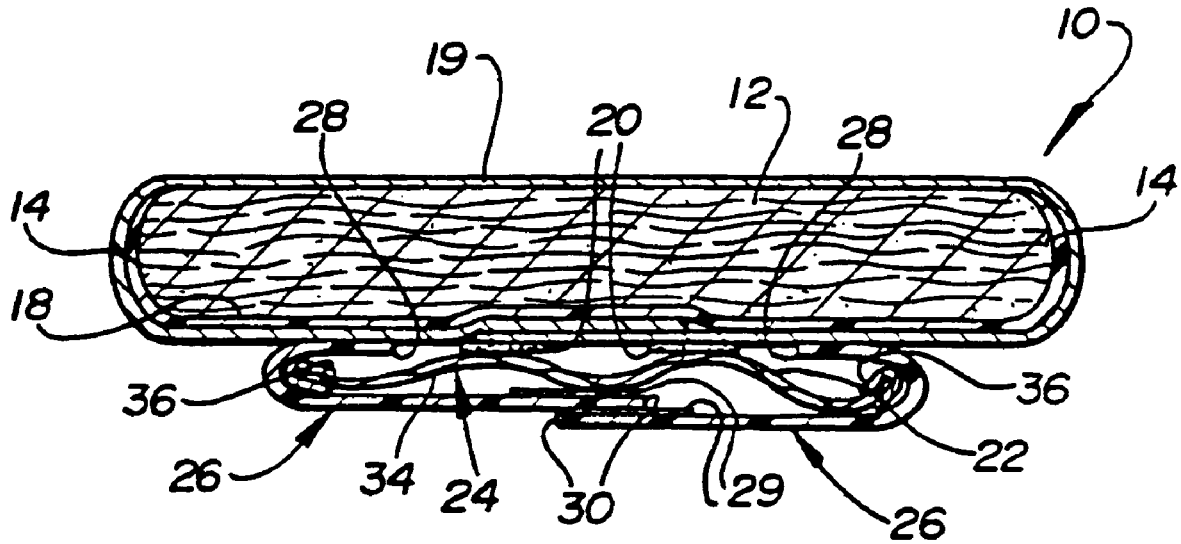

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 7, lines 17–23:

FIG. 9 illustrates yet another embodiment of this invention wherein the flaps each comprise two generally parallel stripes [26'] *426* having an attachment means [34] *429* thereon. Such attachment means could be pressure-sensitive adhesive or alternatively could be any of the well known fastening means such as the so-called ["Velcro" binders,] *"VELCRO" hook and loop fasteners,* buttons, snaps or the like.

AS A RESULT OF REEXAMINATION, IT HAS BEEN DETERMINED THAT:

The patentability of claims 1–7 is confirmed.

New claims 8–15 are added and determined to be patentable.

*8. A sanitary napkin of claim 1 whereby one flap overlaps and affixes to the other flap when said flaps are affixed in said encircling position.*

*9. An improved sanitary napkin comprising a central absorbent element and having generally longitudinally extending edges, a body facing side, a garment facing side, and adhesive means longitudinally disposed about at least a portion of a longitudinal centerline on said garment facing side for adhering the napkin to an inner crotch portion of an undergarment;*

*said napkin having two flaps which are noncontiguous with each other, each affixed at one end thereof to the garment facing side of the napkin with the remainder of the flaps freely extending laterally in a direction transverse to the longitudinally extending edges of the napkin, said flaps being sized and configured to encircle the crotch portion of the undergarment and being provided with means for affixing said flaps in said encircling portion;*

*said flaps being affixed to the garment facing side of the napkin at an affixation point which is inward from the longitudinally extending edges of the napkin;*

*whereby when said flaps are affixed in said encircling position, opposing edges of the undergarment are gathered toward the longitudinal centerline of the napkin, under the napkin and inwardly of the longitudinally extending edges of the napkin, to shield the undergarment edges from body fluids by the garment facing side of the napkin.*

*10. A sanitary napkin of claim 9 whereby one flap overlaps and affixes to the other flap when said flaps are affixed in said encircling position.*

*11. The napkin of claim 9 wherein said affixation point is at least one-eighth inch inward of said longitudinal edge.*

*12. The napkin of claim 9 wherein said affixation point is at least one quarter inch inward of said longitudinal edge.*

*13. An improved sanitary napkin comprising a central absorbent element and having generally longitudinally extending edges, a body facing side, a garment facing side, and adhesive means longitudinally disposed about at least a portion of a longitudinal centerline on said garment facing side for adhering the napkin to an inner crotch portion of an undergarment;*

*said napkin being further provided with two flaps which are noncontiguous with each other, each affixed at one end thereof to the garment facing side of the napkin with the remainder of the flaps freely extending laterally in a direction transverse to the longitudinally extending edges of the napkin, said flaps being affixed to the garment facing side of the napkin at an affixation point which is inward from the longitudinally extending edges of the napkin;*

*said flaps being sized and configured to encircle the crotch portion of the undergarment and being provided with means for affixing said flaps in said encircling portion, such that when said flaps are affixed in said encircling position, opposing edges of the undergarment are gathered toward the longitudinal centerline of the napkin and inwardly of the longitudinally extending edges of the napkin, to shield the undergarment edges from body fluids by the garment facing side of the napkin.*

*14. The napkin of claim 13 wherein said affixation point is at least one-eighth inch inward of said longitudinal edge.*

*15. The napkin of claim 13 wherein said affixation point is at least one quarter inch inward of said longitudinal edge.*

* * * * *